United States Patent [19]

Lillig et al.

[11] Patent Number: 4,965,049
[45] Date of Patent: Oct. 23, 1990

[54] MODULAR ANALYZER SYSTEM

[75] Inventors: John E. Lillig, Diamond Bar; Michael J. Whelan, Anaheim Hills; Thomas V. Cheon, Costa Mesa; Patricia A. Sisson, Santa Ana; Orlando Flores, Anaheim, all of Calif.

[73] Assignee: Beckman Instruments, Inc., Fullerton, Calif.

[21] Appl. No.: 355,799

[22] Filed: May 22, 1989

Related U.S. Application Data

[63] Continuation of Ser. No. 884,464, Jul. 11, 1986, abandoned.

[51] Int. Cl.$^5$ ............... B65B 43/42; G01N 35/02; G01N 35/06
[52] U.S. Cl. ............... 422/68.1; 141/130; 422/63; 422/64; 422/67; 436/43
[58] Field of Search ............... 422/63, 64, 67, 68.1; 141/130; 436/43

[56] References Cited

U.S. PATENT DOCUMENTS

| 3,192,968 | 7/1965 | Baruch et al. | 141/82 |
| 3,193,358 | 7/1965 | Baruch | 23/253 |
| 3,644,095 | 2/1972 | Netheler et al. | 422/65 |
| 3,814,582 | 6/1974 | Rohrbaugh et al. | 23/230 |
| 3,842,679 | 10/1974 | Iwao et al. | 73/431 |
| 4,169,125 | 9/1979 | Rodriquez | 422/65 |
| 4,234,540 | 11/1980 | Ginsberg et al. | 422/64 |
| 4,268,477 | 5/1981 | Herzstark | 422/67 |
| 4,528,159 | 7/1985 | Liston | 422/64 X |
| 4,539,295 | 9/1985 | Blough, Jr. | 436/34 |
| 4,558,946 | 12/1985 | Galle et al. | 422/63 |

OTHER PUBLICATIONS

Hatton et al, Adv. in Lab Automation Robotics 1985 pp. 621-635.
Hawk et al; Advances in Laboratory Automation Robotics 1984; Zymark Corp., Inc., 1984 pp. 40 and 50.
Ostling, *Chem. Instrumentation*, 5(1) pp. 1-20 (1973-1974).

*Primary Examiner*—Robert J. Warden
*Assistant Examiner*—Kimberly A. Trautman
*Attorney, Agent, or Firm*—William H. May; Arnold Grant; Gary T. Hampson

[57] ABSTRACT

A system of modular analyzers each adapted for independent operation and each possessing different operational characteristics adapted for particular applications. Such modular analyzers may be joined together with precise indexing means such that a single sample carousel may be accessed by fluid transfer probes from both of the analyzers to thus form a system which operates as a single analyzer of increased capacity and versatility.

13 Claims, 5 Drawing Sheets

MODULAR ANALYZER SYSTEM

This is a continuation of co-pending application Ser. No. 06/884,464 filed on July 11, 1986 now abandoned.

Background

The present invention relates generally to the field of clinical chemistry and more particularly to clinical chemistry analyzers suitable for use in hospitals, and commercial laboratories.

A number of clinical chemistry analyzers are available in the art. Such analyzers vary from simple, essentially manually operated instruments to complex, highly automated analyzers.

Each analyzer has its own particular performance characteristics related to the number or menu of different tests that the analyzer can perform, the number of samples that may be placed onto the analyzer, and the number of samples that can be processed in a given period of time, or "throughput." Often, analyzers that provide rapid sample analysis offer a relatively limited menu of tests. Conversely, other analyzers, sometimes referred to as random access analyzers, may offer a much larger menu of tests but have a correspondingly decreased sample throughput.

The high volume, limited menu analyzers described above frequently offer a menu directed to those tests or chemistries that are most commonly performed for patient samples, such as sodium, potassium, glucose, creatinine, BUN, and the like. In comparison, the large menu, lower throughput analyzers may well offer such high demand chemistries but also offer chemistries that are required on a relatively infrequent basis.

A clinical chemistry laboratory may, for example, require a high throughput, limited menu analyzer, preferring to use the services of commercial laboratories for low demand tests, or performing low demand tests using complementary general purpose instruments. The requirements of the laboratory, however, may change with time. An initial need to perform only limited menu, high volume tests on an automated analyzer may well expand to additionally require automated analysis of low-demand tests where the costs or inconvenience of commercial laboratories become great or where the volume of low-demand tests overwhelms the capabilities of general purpose instruments.

One solution to this problem is to simply install a second separate automated analyzer to satisfy the new demand. However, an additional analyzer requires additional operating personnel, separate sample preparation and loading, separate test selection and programming, and the collation of separate test results for samples drawn from the same patient. All of these drawbacks lead to increased laboratory operating expenses, a particular disadvantage in light of today's ever-increasing awareness of health care cost containment.

Summary of the Invention

The system of the present invention overcomes the limitations and disadvantages noted above, providing a modular system of clinical chemistry analyzers each having unique operating characteristics directed to particular combinations of menu size and sample throughput. Such analyzers may be operated individually and separately to meet particular laboratory needs or may be advantageously combined to form a single analyzer possessing the attributes of the individual modules. When combined to form a broad-capability analyzer, such analyzer utilizes a single sample loading system and need only be programmed to select the tests for a particular sample, regardless of which module performs the tests. Accordingly, analyzer operation is simplified and streamlined, decreasing costs and saving floor space within the clinical laboratory facility.

A system in accordance with the present invention includes at least a first and second analyzer each including sample carousels, analyzing means, and automated probe means for transferring samples from the sample carousels to the analyzing means. Each of the analyzers also includes indexing and joining means for precisely joining the first and second analyzers and indexing the first analyzer automated probe with respect to the second analyzer sample carousel. Control means in one of the first or second analyzers synchronizes and controls the first analyzer automated probe means, the second analyzer automated probe means and the second analyzer sample carousel so that the automated probe means for both the first and second analyzers can access samples received in and carried by the second analyzer sample carousel. Preferably, the sample carousel in the first analyzer is removed and sample volumes for the first analyzer are obtained from the sample carousel of the second analyzer.

Detailed Description

Figure 1:
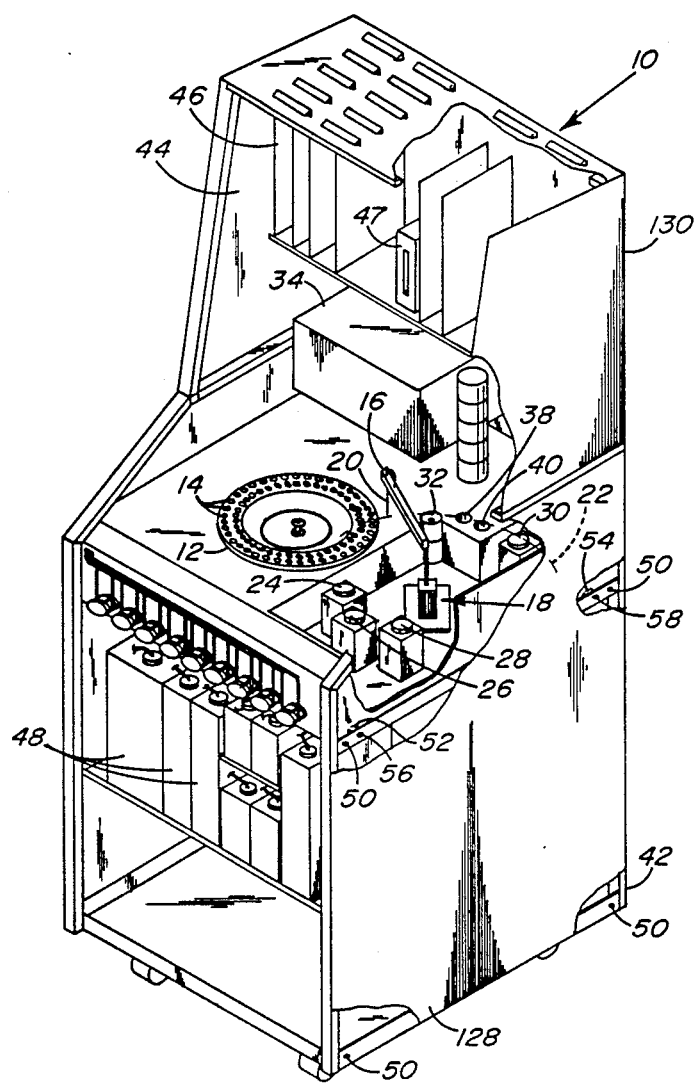
FIG. 1 is an isometric view of a first modular analyzer in accordance with the system of the present invention.

With reference to FIG. 1, a modular analyzer 10 in accordance with the present invention is a limited-menu high-throughput analyzer. The modular analyzer 10 includes a sample carousel 12 which includes a plurality of sample receiving wells 14 disposed in circular concentric rows near the periphery of the carousel 12. The carousel 12 may be removed from the modular analyzer 10 for loading of samples into the wells 14 in a conventional fashion. The sample carousel 12 includes means for rotation such as, for example, a stepper motor so as to position the wells 14 for removal of sample therefrom.

A sample arm 16 is supported at one end by a displacement mechanism 18 for raising and lowering the arm 16 and rotating the arm 16 about the mechanism 18 in a conventional fashion. The sample arm 16 supports a probe 20 which describes an arc 22 over the working surface of the modular analyzer 10. More particularly, the arc 22 passes over sample pickup stations above the inner and outer rows of the sample receiving wells 14 so that samples from wells in either of the rows may be withdrawn into the probe 20. The arc 22 also passes over four analysis modules 24, 26, 28, 30 of a conventional design. Each of the modules 24, 26, 28, 30 includes a sample receiving port and is adapted to receive sample volumes from the probe 20 and perform analyses thereon. The modules 24, 26, 28, 30 may be similar to, for example, various of the modules included in the ASTRA ® Analyzer from Beckman Instruments, Inc. of Brea, California.

The arc 22 also swings over a sample injection cell 32 adapted to receive sample volumes from the probe 20 and flow such volumes to a flow analysis module 34 capable of analyzing "electrolytes" including chloride, sodium, potassium, and CO2. The flow analysis module 34 may be similar to the flow analysis techniques used in the E4A ™ Analyzer from Beckman Instruments, Inc., of Brea, California. The sample injection cell 32 includes means for sealing the probe 20 therein while sample volumes are injected from the probe 20 into the cell 32.

The modular analyzer 10 also includes locations about the arc 22 for wells 38 and 40 adapted to receive calibration reagents which may be required for calibration of various of the modules 24, 26, 28, 30, 34.

The working surface of the modular analyzer 10 is supported by means of a frame 42. The frame 42 also supports an electronics card cage 44 which includes a plurality of circuit boards 46, a disk drive 47, and related electronic circuitry for controlling the modular analyzer 10. Fluid reservoirs 48 contain reagents for use in the modules 24, 26, 28, 30, 34. A conventional computer terminal, including a keyboard and CRT, and a printer (not shown) are connected to the electronic circuitry included in the card cage 44 for providing operating instructions to, as well as receiving results from, the modular analyzer 10, all in a conventional fashion.

The modular analyzer 10 as described above is thus a high-throughput, limited-menu analyzer of the type known in the art which is adapted to perform parallel analyses concurrently in the modules 24, 26, 28, 30, 34 for a sample volume drawn from the sample carousel 12. The operating cycle of the modular analyzer 10 generally includes drawing a sample volume from the sample carousel 12 into the probe 20, rotating the arm 16 to the sample injection cell 32 and injecting a portion of the sample volume into the cell 32 for analysis by the flow analyzer module 34. The arm 16 raises the probe 20 and rotates the probe 20 along the arc 22 to deposit portions of the sample volume to the analyzer modules 24, 26, 28, 30 for individual analysis therein. The probe 32 is then moved to the cell 32 for washing the probe tip and to complete the analysis and calibration cycle for the flow analysis module 34, preparing the modular analyzer for the next operation cycle.

The modular analyzer 10 is adapted in accordance with the present invention to operate as a portion of a system of modular analyzers. More particularly, the frame 42 includes a plurality of holes 50, index plates 52, 54, and holes 56, 58 in such plates 52, 54. Each of the index plates 52, 54 is precisely located with respect to the displacement mechanism 18 and the arc 22 described by the probe 20. The holes 50 are placed in the frame 42 proximate a side 59 of the modular analyzer 10 nearest the displacement mechanism 18. The portion of the frame 42 through which the holes 50 pass defines a plane that is a predetermined distance from the displacement mechanism 18. Further in accordance with the present invention, the displacement mechanism 18 is adapted to extend the probe travel arc 22 beyond the side 59 to a position that is outside of the frame 42.

Figure 2:
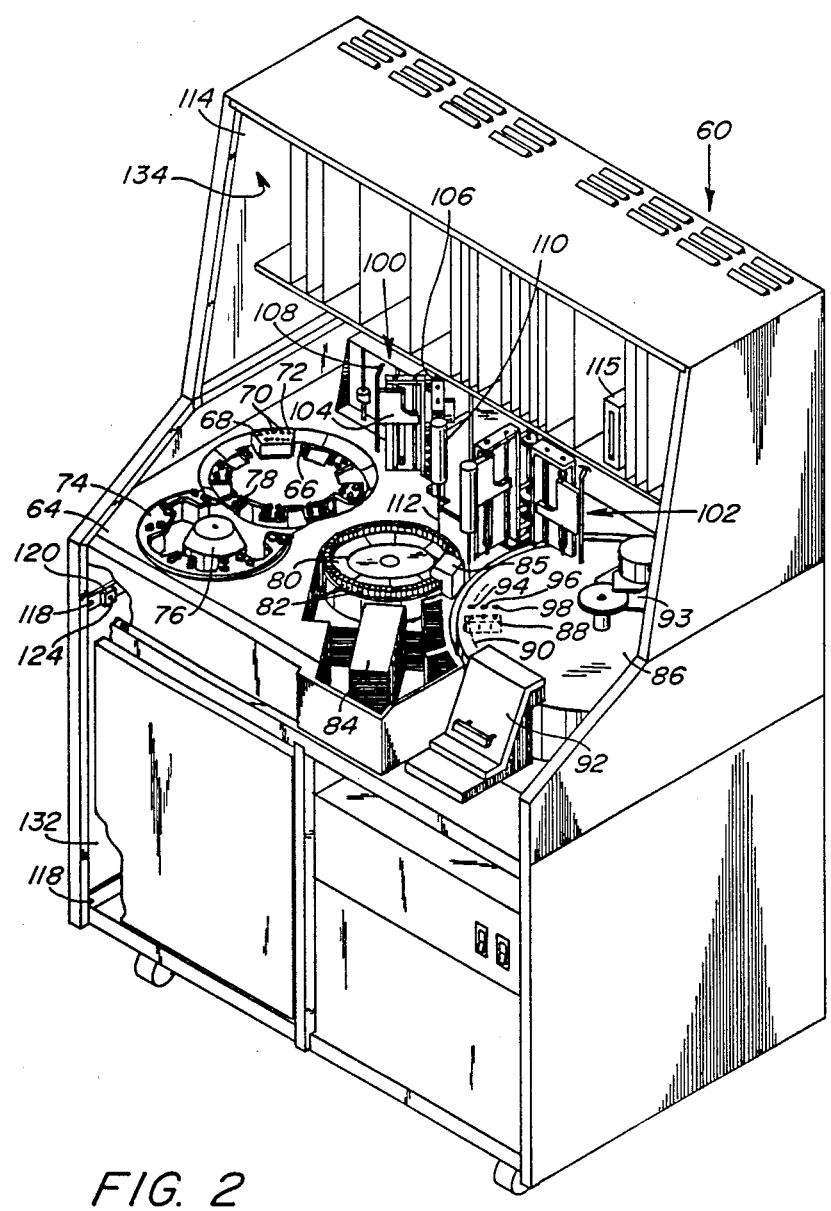
FIG. 2 is an isometric view of a second modular clinical analyzer in accordance with the system of the present invention.

With reference now to FIG. 2, a large menu, random access clinical modular analyzer 60 is shown therein. The modular analyzer 60 includes a frame 62 supporting a working surface 64. The working surface 64 includes a sample carousel 66 adapted to receive a plurality of sample sectors 68, each of the sectors 68 including ten openings 70 therein each for receiving a sample cup 72. The sample carousel 66 is automatically rotated by means of, for example, a stepper motor as is well known in the art.

The sample sectors 68 are loaded onto the modular analyzer 60 at a loading tray 74. The loading tray 74 includes a transfer mechanism 76 which transfers one sample sector 68 from the loading tray 74 to a transfer position 78 and simultaneously transfers a sample sector 68 at the transfer position to the loading tray 74. In the embodiment disclosed herein, the transfer mechanism 76 operates by lifting the sample sectors 68 on the loading tray 74 and at the transfer position 78 up and above the sample sectors 68 on the sample carousel 66. The transfer mechanism 76 then steps one sector position clockwise as seen from above in FIG. 2, lowering the sample sectors back onto the loading tray 74 and onto the sample carousel 68 at the transfer position 78.

The working surface 64 also supports a reaction wheel 80 which in turn carries a plurality of sample cuvettes 82 about its periphery. The reaction wheel 80 is rotated by means of a stepper motor that is controlled in response to the system electronics and control circuitry. A flash photometer 84 at the periphery of the reaction wheel 80 cooperates with the wheel 80 to direct light through the cuvettes 82 as the reaction wheel 80 is rotated. In the embodiment disclosed herein, the reaction wheel 80 may support eighty cuvettes 82 and be controlled so as to intermittently rotate at approximately ninety RPM during which time the flash photometer 84 operates to obtain polychromatic colorimetric data for the fluids carried within the cuvettes 82. A cuvette wash station 85 also at the periphery of the reaction wheel 80 washes the cuvettes 82 to clean and prepare the cuvettes 82 for another analysis.

A refrigerated storage compartment 86 contains a plurality of reagent cartridges 88 supported by a reagent carousel 90. Each of the cartridges 88 includes three separate compartments adapted to hold reagents for a particular test or chemistry performed by the modular analyzer 60. The reagent cartridges 88 may be placed onto and removed from the reagent carousel 90 via a front door 92 in the compartment 86. The compartment 86 includes a rotational mechanism 93 for rotating the reagent carousel 90 so as to position one of the reagent cartridges 88 under three openings 94, 96, 98 formed in the top of the compartment 86. The openings 94, 96, 98 allow access to the reagent cartridges 88 for removal of reagent therefrom.

The working surface 64 also supports a sample transfer and stirring mechanism 100 and a reagent transfer and stirring mechanism 102. Preferably, the sample transfer and stirring mechanism 100 includes a fluid probe assembly 104 pivoted about a pivot point 106. A probe 108 is carried by the assembly 104. The assembly 104 is adapted to withdraw a predetermined sample volume from a sample sector 68, raise the probe 108 above the sample sector 68, pivot the probe 108 to a sample injection position above a predetermined cuvette 82 on the reaction wheel 80, lower the probe 108 to the cuvette 82, and dispense the predetermined sample volume therein.

The mechanism 100 also includes a stirring assembly 110 supporting a motorized stirring rod 112 that may be swung into position over the cuvette into which sample has been injected. The stirring assembly 110 lowers the stirring rod 112 into the cuvette and the rod is rotated to stir the contents of the cuvette Similarly, the reagent transfer and stirring mechanism 102 includes a reagent fluid probe assembly and a stirring assembly similar to those just described. The reagent fluid probe assembly is adapted to swing the reagent probe in an arc over the openings 94, 96, 98, lower the probe through the appropriate opening into a reagent cartridge 88, withdraw reagent into the probe, elevate and move the probe over a cuvette on the reaction wheel positioned at a reagent injection station, lower the probe into the cuvette 82 and inject reagent into the cuvette 82.

Both the sample and reagent transfer and stirring mechanisms 100 and 102 also pass over wash stations for washing the respective probes and stirring rods. The mechanisms 100 and 102, as well as the associated wash stations, are controlled automatically in fashions that are well known in the automated clinical analyzer art.

The modular analyzer 60 also includes a card cage 114 which holds a disk drive 115 and a plurality of circuit boards containing the control and analysis electronics for the modular analyzer 60. A conventional computer terminal including a keyboard and CRT, as well as a printer (not shown), are connected to the control and analysis electronics for providing test and operating instructions to the modular analyzer 60. Such instructions may include, for example, patient name, patient ID number, sample sector ID numbers, and the tests that are to be performed for samples carried by the identified sample sectors. The terminal and printer also receive and display the results of tests performed by the modular analyzer 60.

Although a particular embodiment of an modular analyzer 60 has been described above, it is to be recognized that the modular analyzer 60 is merely an example of a large-menu, reduced throughput clinical analyzer of a type well known in the art. In the embodiment disclosed herein, the modular analyzer 60 performs repeated operating cycles each including sample and reagent addition to cuvettes and rotations of the reaction wheel 80 to thus provide serial analyses of samples on the reaction wheel 80. Briefly, the modular analyzer 60 is controlled to deposit reagents into a cuvette 82. With repeated operating cycles, the reaction wheel 80 advances the cuvette 82 around the reaction wheel 80 until a sample is added to the cuvette 82 and the analysis is performed using the photometer 84 to obtain data as described above. Additional operating cycles advance the cuvette through the wash station 85, preparing it for a subsequent analysis. The analysis data is processed by the control and analyzers electronics to provide test results via the terminal and/or printer.

In accordance with the present invention, the frame 62 includes four holes 118 (only two of which are shown) formed therethrough. Two index plates 120 (only one of which is shown) are fixed to the frame 62 proximate the front and rear vertical members thereof. Each of the index plates 120, 122 includes holes 124, formed therethrough precisely located with respect to the central axis and horizontal operating plane of the sample carousel 66. The portion of the frame 62 though which the holes 118 pass defines a plane that is a predetermined distance from the central vertical axis of the sample carousel 66. The position of the holes 118 and 124 are a mirror image of the holes 50 and 56, 58 in the modular analyzer 10. Furthermore, the card cage 114 is adapted to include an interface card functioning as described hereinbelow.

Figure 3:
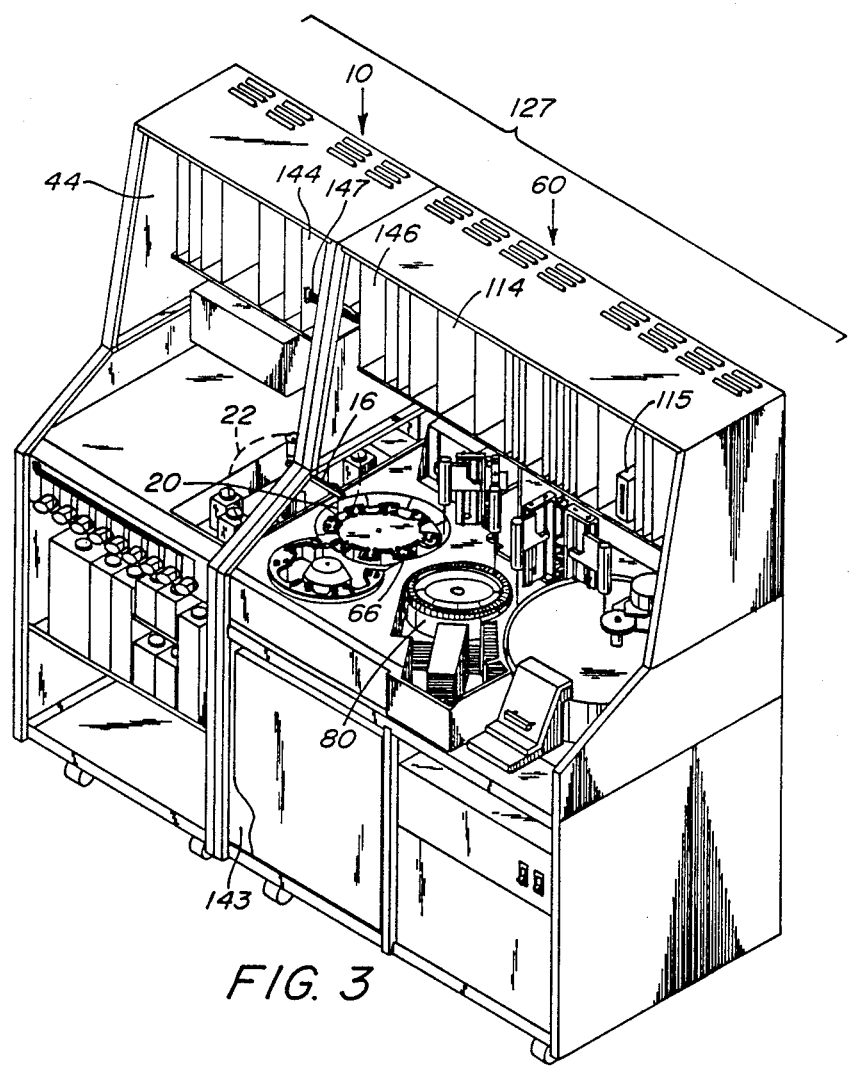
FIG. 3 is a clinical analyzer formed using the modules of FIGS. 1 and 2.

The individual modular analyzers 10 and 60 may be operated independently to perform clinical chemistry tests, addressing certain distinct capacity, menu and throughput capabilities needed in clinical chemistry laboratories. Advantageously, the analyzers 10 and 60 may be uniquely joined to form a single clinical chemistry system 127 (FIG. 3) possessing the attributes of both of the analyzers 10 and 60 while significantly decreasing operator workload and involvement as compared to two separate analyzers.

Figure 3A:
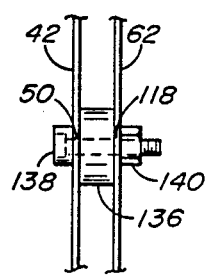
FIGS. 3A and 3B are side views of means for joining modules as shown in FIG. 3.
Figure 3B:
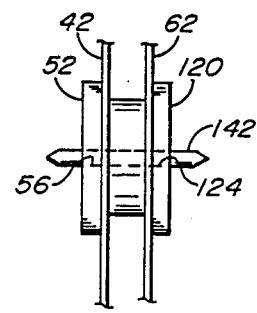

More particularly, side panels 128 and 130 on the right side of the modular analyzer 10 as viewed in FIG. 1. may be removed from the modular analyzer 10. Side panels 132 and 134 on the left side of the modular analyzer 60 as is seen in FIG. 2. similarly removed from the modular analyzer 60. As seen with reference to FIG. 3, the modular analyzers 10 and 60 are positioned side-by-side. Spacers 136 are placed between the holes 50 and 118 in the modular analyzers 10 and 60 (FIG. 3A) and are retained by bolts 138 and nuts 140. Locating pins 142 are inserted into the holes 56, 58, and 124 within the corresponding index plates 52, 54, and 120. A false panel 143 is installed between the modular analyzers 10 and 60 to maintain separate cooling air flow within the repective modular analyzers 10 and 60

The spacers 136 provide a precise parallel spacing relationship between the planes defined by the frames 42 and 62 through which the holes 50 and 118 are formed. The locating pins 142 provide precise vertical and horizontal alignment of the frames 42 and 62.

The predetermined relationship between the frame 42 and the index plates 52 and 54 with respect to the displacement mechanism 18 and probe 20 as well as the predetermined relationship between the frame 62, plates 120, 122 and the sample carousel 66 allow the sample arm 16 to swing the probe 20 along the ar 22 from the modular analyzer 10 into the modular analyzer 60 to selected sample aspiration or pickup locations above the sample carousel 66. Thus the probe 20 can access samples carried by the sample carousel 66. With all samples for the modular analyzer 10 coming from the sample carousel 66, the sample carousel 12 is removed from the modular analyzer 10.

Figure 4:
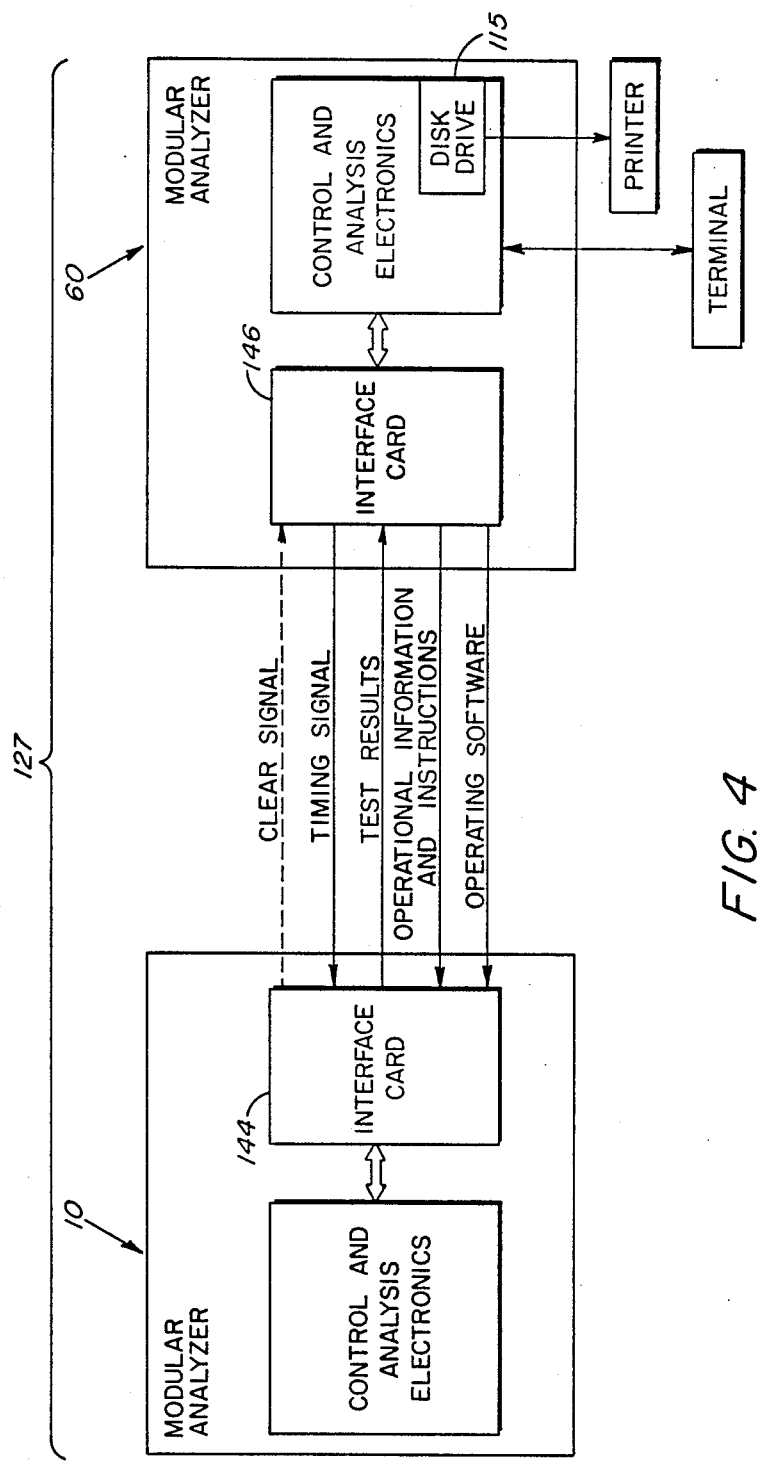
FIG. 4 is a functional block diagram of electronic interface signals provided between modular analyzers forming the system of FIG. 3.

Electronic, electrical and fluid interfaces are also provided between the analyzers 10 and 60 to form the system 127. Interface circuit cards 144 and 146 are installed into the card cages 44 and 114 and suitable cabling 147 is connected therebetween. The disk drive 47 in the analyzer is removed. The interface cards provide suitable electronic interfaces between the electronics installed in the card cages 44 and 114. Specifically, interface card 146 provides program, data and timing signals via the cabling 147 to the card 144. As seen with reference to the block diagram of FIG. 4, the program and data signals include operational information and instructions entered into the modular analyzer 60 through the disk drive 115 or the terminal connected thereto. For example, such operational information and instructions include the identification and location of samples on the sample carousel 66 that require analysis by the modular analyzer 10. The data signals also identify the tests to be performed for such samples and instruct the control circuitry in the card cage 44 to displace the sample arm to the sample carousel 66 for sample pickup. Operating software for one or more microprocessors in the modular analyzer 10 may be loaded from the disk drive 115 through the interface cards 146 and 144 to suitable memory means within the modular analyzer 10.

The cards 144 and 146 also allow the results of tests performed by the modular analyzer 10 to be relayed to the modular analyzer 60. The results may be sorted by, for example, sample ID or patient ID number, combined with results produced by the modular analyzer 60, and displayed on the terminal or printed on the printer connected to the modular analyzer 60. Because all test identification and operational control for the system 127 is made via the terminal and printer connected to the modular analyzer 60, the terminal and printer connected to the modular analyzer 10 may be removed.

The timing signal transmitted from the card 146 to the card 144 synchronizes the operation of the modular analyzer 10 with the modular analyzer 60. A timing signal may be provided to the modular analyzer 10 indicating that the sample arm 16 may swing into the modular analyzer 60 and fill the probe 20 with sample from one of the sample aspiration or pickup locations on the sample carousel 66. Such timing pulse indicates that the sample carousel 66 will be stationary during the time that the probe 20 aspirates sample from the carousel 66. The modular analyzer 60 controls the sample carousel 66 to remain steady during the aspiration period.

Also, the modular analyzer 10 may provide a clear signal or timing pulse from the card 144 to the card 146 informing the modular analyzer 60 that the probe 20 has been withdrawn from the sample carousel 66, whereupon the carousel 66 may be controlled to service sector loading and unloading functions or sample aspiration by the sample fluid probe assembly 104. Preferably, the timing pulse provided to the modular analyzer 10 to initiate the sample aspiration cycle coincides with a time period during which the sample carousel 66 would otherwise be idle during the operating cycle of the modular analyzer 60.

The electronic interface signals described above may be provided between the modular analyzers 10 and 60 in a conventional fashion. For example, the modular analyzers 10 and 60 may both include the same microcomputer bus structure that is interconnected by the interface cards 144 and 146. Thus, software, operating information, test results and the timing and clear signals maybe transferred between the microcomputer bus in each of the modular analyzers 10 and 60 via the interface cards 144 and 146. The control and analysis electronics in the modular analyzer 60 may also directly access the microcomputer bus within the modular analyzer 10 for the transfer of data or instructions, all in a conventional fashion.

Figure 5:
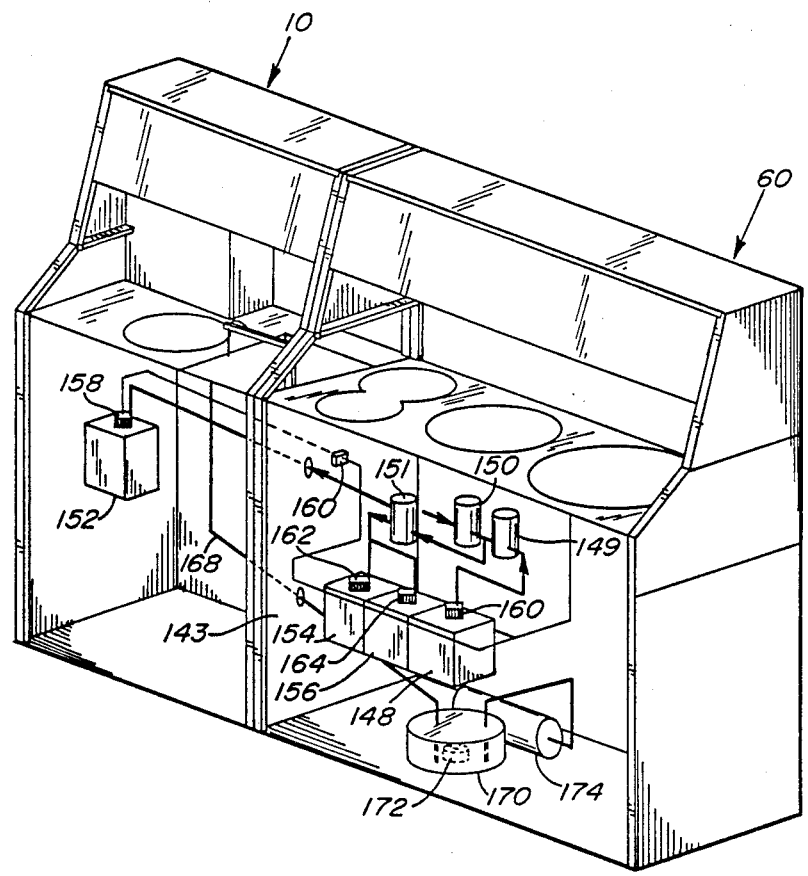
FIG. 5 is a simplified wash fluid diagram for the analyzer of FIG. 3.

The modular analyzers 10 and 60 share a common source of wash fluid in the system 127 (FIG. 5). Concentrated wash solution from a reservoir 148 is supplied to a valve 149 and deionized water from a suitable source is applied to a similar solenoid valve 150. The outputs of the valves are connected at a T connection to a solenoid controlled diverter valve 151 which either supplies diluted wash solution to a reservoir 152 in the modular analyzer 10 or to reservoirs 154, 156 in the modular analyzer 60. A fluid level sensor 158 senses the level of wash fluid in the reservoir 152. The sensor is connected through the false panel 143 via connector 160 to a bus carrying signals from level sensors 160, 162 and 164 on each of the reservoirs 148, 154 and 156. The signals from the sensors 158, 160, 162, 164 are applied to the control electronics in the card cage 114. The control electronics, is response to the level sensors 158, 160, 162, 164, control the valves 149-151 to replenish diluted wash solution in the reservoirs 158, 160, 162, 164.

A wash fluid drain line 168 is connected from the modular analyzer 10 through the false panel 143 into a drain reservoir 170 which also holds used wash fluid from the modular analyzer 60 delivered by a drain line. A sensor 172 in the reservoir 170 detects the level of the used wash fluid therein, activating a pump 174 to drain the reservoir 170 to an external drain line as required to maintain the wash solution within the reservoir 170 below a predetermined level.

The wash fluid and drain systems just described thus combine such functions for both the modular analyzers 10 and 60, requiring that only a single wash fluid concentrate reservoir 148 be filled by an operator as required and further reducing the number of drain lines needed to service the system 127.

In operation, samples carried in sample sectors 68 to be tested by the system 127 are placed onto the loading tray 74. The operator of the system 127 instructs the system 127 as to the tests that are to be performed for each of the samples via the terminal connected to the modular analyzer 60. The operator may identify the tests without regard to whether the tests are to be performed on the modular analyzer 10 or the modular analyser 60. The modular analyzer 60 operates as described above to move the sample sector 68 from the loading tray to the sample carousel 66.

The modular analyzer 60 sorts the tests requested as to whether such tests are to be performed by the modular analyzer 10 or the modular analyzer 60. The sorting may be carried out, for example, on the basis of preprogrammed instructions that automatically assign all tests to the modular analyzer 10 that are on the modular analyzer 10 menu, or may be carried out in response to specific instructions from the operator. The modular analyzer 60 transfers this test information, as well as the sample aspiration location above the sample carousel 66, to the modular analyzer 10 via the interface cards 146 and 144. The modular analyzer 60 retains the identity of the samples for analysis by the modular analyzer 10 as well as the location of such samples on the sample carousel 66.

The timing signal transmitted from the modular analyzer 60 to the modular analyzer 10 establishes synchronization between the modular analyzers 10 and 60. For example, in the embodiment disclosed herein, the overall operating cycles of the modular analyzers 10 and 60 are synchronized in that a sample may be withdrawn from the sample carousel every fifteen seconds by the sample fluid probe 108 and may be withdrawn every fourty five seconds by the probe 20. Thus, three operating cycles of the modular analyzer 60 are performed for every one operating cycle of the modular analyzer 10. Prior to the timing signal, the modular analyzer 60 positions the sample carousel 66 such that the required sample is disposed beneath one of the sample aspiration locations on the sample carousel 66. Upon receipt of the timing signal, the sample arm 16 operates as described above to move from the modular analyzer 10 into the modular analyzer 60 and over the sample carousel 66.

The probe 20 is lowered into the specified sample aspiration location, sample is withdrawn, and the sample arm 16 swings back into the modular analyzer 10 to distribute the sample to the analysis modules 24, 26, 28, 30, 34. The operation of the sample carousel 66 then continues as required by the modular analyzer 60. This synchronized operation of the modular analyzers 10 and 60 continues to thus provide rapid analyses of samples for each operating cycle of the modular analyzer 10 and the serial analysis of samples performed by repeated operating cycles of the modular analyzer 60.

Thus, the system of the present invention presents a unique advance in the state of the clinical chemistry art, enabling a clinical chemistry analytical system to be tailored to the needs of a clinical laboratory. A clinical laboratory may intially purchase one of the modular analyzers to minimize initial investment and may expand their initial modular analyzer in the future at modest cost and without the inconvenience of extensive operator training or increase in operator workload. Each of the modular analyzers may have similar operating instructions and commands (including the content of the "pages" or "screens" displayed on the terminals and the order in which such screens are presented, the method by which the operator selects tests, and the way that patient and sample identification information is entered) so that an operator trained on one of the modular analyzers can easily adapt to another of the modular analyzers.

Advantageously, the modular analyzers may be joined to form a system comprising the attributes of both modular analyzers. Samples need be loaded at only one sample loading position on the system and instructions for the system are entered by an operator via a single terminal that allows the operator to enter instructions for the system as a whole regardless of which analyzer module performs the tests. The result is simplified operation, versitility, descreased operating and training costs, and a compact system that saves space in a clinical laboratory.

It will be appreciated that although particular embodiments of the present invention have been disclosed herein, the invention is not to be limited by such embodiments but is to be afforded the full scope of the claims appended hereto.

We claim:

1. In a clinical chemistry analyzer system, comprising:

a first modular analyzer including a sample carousel adapted to receive a plurality of samples, analyzing means for analyzing the samples and automated probe means for transferring samples from the sample carousel to the analyzing means;

a second modular analyzer including a second sample carousel adapted to receive a plurality of samples, an analyzing means in the second modular analyzer different from the analyzing means of the first modular analyzer for analyzing samples, and a second automated probe means for transferring samples from the second sample carousel to the analyzing means of the second modular analyzer, the improvement being:

indexing and joining means for selectively precisely joining the first modular analyzer to the second modular analyzer and indexing the first modular analyzer to the second modular analyzer and indexing the first modular analyzer automated probe means with respect to the second modular analyzer sample carousel, and control means for synchronizing and controlling the first modular analyzer automated probe means and the second modular analyzer sample carousel such that the first modular analyzer automated probe means accesses samples received in and carried by the second modular analyzer sample carousel, the first automated probe means selectively transferring the accessed samples to the analyzing means of the first modular analyzer whereby the first independent modular analyzer and second independent modular analyzer selectively constitutes a single interdependent system.

2. A system as in claim 1 wherein the first modular analyzer sample carousel includes means for removably retaining said sample carousel on the first modular analyzer.

3. A system as in claim 1 wherein the first modular analyzer automated probe means is carried by a displacement mechanism rotatable about a pivot point, and wherein the first modular analyzer includes a working surface which includes at least the sample carousel and the analyzing means, and the displacement mechanism includes means for moving said automated probe means about the pivot point such that the first modular analyzer automated probe means describes an arc about the pivot point that extends beyond the working surface of the first modular analyzer.

4. A system as in claim 3 wherein the arc extends over a sample pickup station on the first modular analyzer sample carousel, sample receiving ports for the first modular analyzer analyzing means, and a sample pickup location over the second modular analyzer sample carousel.

5. A system as in claim 1 wherein the indexing and joining means includes spacers between the first and second modular analyzers, index holes located in structures of the first and second modular analyzers and being precisely related with respect to the first modular analyzer automated probe means and the second modular analyzer sample carousel, and pins fitted into such holes for indexing the first modular analyzer automated probe means with respect to the second modular analyzer sample carousel.

6. An analyzer system as claimed in claim 1 wherein the first modular analyzer is selectively operable independently or as a first modular analyzer in an interdependent system which includes a first modular analyzer and a second modular analyzer, said first modular analyzer comprising:

a first sample carousel adapted to receive a plurality of samples, a first analyzing means for analyzing the samples, a first automated probe means for transferring samples from the first sample carousel to the first analyzing means, such first automated probe means including means for rotating the first automated probe means beyond a removable side panel of the first modular analyzer, and indexing means precisely positioned on the first modular analyzer, with respect to the first automated probe means, whereby the first modular analyzer can be indexed with a second modular analyzer in the system with the first automatic probe means precisely indexed for the second modular analyzer.

7. An analyzer as in claim 6 wherein the indexing means includes a frame defining a plane in a predetermined position with respect to the first automated probe means and a plurality of index plates each including holes in a predetermined relationship with respect to the first automated probe means.

8. An analyzer system as claimed in claim 1 wherein the first modular analyzer is selectively operable independently, or as a first modular analyzer in an interdependent system which includes a first modular analyzer and a second modular analyzer, said first modular analyzer comprising: a first sample carousel adapted to receive a plurality of samples and indexing with joining means positioned on the first modular analyzer with respect to the first sample carousel, whereby the first modular analyzer can be selectively locatingly indexed and joined with the second modular analyzer in the system with the first sample carousel locatingly indexed for the second modular analyzer.

9. An analyzer as in claim 8 wherein the indexing means includes a frame defining a plane in a predetermined relationship with respect to the first sample carousel and a plurality of index plates each including holes in a predetermined relationship with respect to the first sample carousel.

10. A system as in claim 1 wherein the first modular analyzer is a limited-menu parallel analysis analyzer and the second modular analyzer is a broad-menu, limited throughput analyzer.

11. A system as in claim 1 wherein the first modular analyzer includes means for selectively removing the sample carousel on the first modular analyzer, whereby on removal the area previously occupied by the sample carousel is replaced with working surface flat panel.

12. A system as claimed in claim 1 wherein an analyzer is selectively operable independently or as a first modular analyzer in an interdependent system which includes first modular analyzer and a second modular analyzer, comprising: a first sample carousel adapted to receive a plurality of samples with indexing means precisely positioned on the first modular analyzer with respect to the first sample carousel, whereby the first modular analyzer can be indexed with the second modular analyzer in the system with the first sample carousel precisely indexed for the second modular analyzer, both the first modular analyzer and the second modular analyzer having an automated probe means for transferring samples from the first sample carousel to analyzing means in each respective modular analyzer, and additionally the first sample carousel of the first modular analyzer is indexed for the probe means of the second modular analyzer.

13. An analyzer as in claim 12 wherein the indexing means includes a frame defining a plane in a predetermined relationship with respect to the first sample carousel and a plurality of index plates each including holes in a predetermined relationship with respect to the first sample carousel.

* * * * *

UNITED STATES PATENT AND TRADEMARK OFFICE
CERTIFICATE OF CORRECTION

PATENT NO. : 4,965,049
DATED : October 23, 1990
INVENTOR(S) : Lillig, et al.

It is certified that error appears in the above-identified patent and that said Letters Patent is hereby corrected as shown below:

Column 5, line 65, reads "120, 122" should read -- 120 --

Column 6, line 22, reads "in Fig. 2 similarly" should read
    -- in Fig. 2 are similarly --

Column 6, line 43, reads "along the ar 22" should read
    -- along the arc 22 --

Signed and Sealed this

Sixth Day of October, 1992

Attest:

DOUGLAS B. COMER

*Attesting Officer*  *Acting Commissioner of Patents and Trademarks*